(12) United States Patent
Keach

(10) Patent No.: US 12,702,436 B2
(45) Date of Patent: Aug. 11, 2026

(54) ENDOSCOPIC TRANSLUMINAL STENT ACCESS AND DELIVERY SYSTEM

(71) Applicant: W. L. Gore & Associates, Inc., Newark, DE (US)

(72) Inventor: David C. Keach, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 225 days.

(21) Appl. No.: 18/103,761

(22) Filed: Jan. 31, 2023

(65) Prior Publication Data

US 2023/0172626 A1 Jun. 8, 2023

Related U.S. Application Data

(63) Continuation of application No. 15/963,417, filed on Apr. 26, 2018, now Pat. No. 11,589,884.

(60) Provisional application No. 62/491,356, filed on Apr. 28, 2017.

(51) Int. Cl.

| | |
|---|---|
| ***A61B 17/32*** | (2006.01) |
| ***A61B 17/11*** | (2006.01) |
| ***A61B 17/34*** | (2006.01) |
| *A61B 17/00* | (2006.01) |

(52) U.S. Cl.

CPC .. *A61B 17/320016* (2013.01); *A61B 17/1114* (2013.01); *A61B 17/3478* (2013.01); *A61B 17/3496* (2013.01); *A61B 2017/00252* (2013.01); *A61B 2017/00278* (2013.01); *A61B 2017/1103* (2013.01); *A61B 2017/1139* (2013.01); *A61B 2017/320056* (2013.01); *A61B 2017/346* (2013.01); *A61B 17/3468* (2013.01)

(58) Field of Classification Search

CPC ........ A61B 17/320016; A61B 17/1114; A61B 17/3496; A61B 17/3468; A61B 17/11; A61B 2017/1103; A61B 2017/1139; A61B 2017/320056; A61B 2017/1107; A61B 2017/1135

See application file for complete search history.

(56) References Cited

U.S. PATENT DOCUMENTS

| | | | |
|---|---|---|---|
| 5,792,158 | A | 8/1998 | Lary |
| 6,030,402 | A | 2/2000 | Thompson et al. |
| 8,357,193 | B2 | 1/2013 | Phan et al. |
| 8,454,632 | B2 | 6/2013 | Binmoeller et al. |
| 9,364,259 | B2 | 6/2016 | Lunsford et al. |

(Continued)

FOREIGN PATENT DOCUMENTS

| | | | |
|---|---|---|---|
| CN | 2561432 | Y | 7/2003 |
| JP | 2004-057794 | A | 2/2004 |

(Continued)

OTHER PUBLICATIONS

International Preliminary Report on Patentability received for PCT Patent Application No. PCT/US2018/029768, mailed on Nov. 7, 2019, 6 pages.

(Continued)

*Primary Examiner* — Katherine M Rodjom

(57) ABSTRACT

Aspects of the present disclosure are directed toward apparatuses, systems, and methods for stent access and device delivery. In certain instances, the apparatuses, systems, and methods may include a plurality of struts arranged about the one or more cutting blades on a tip portion.

20 Claims, 10 Drawing Sheets

(56) References Cited

U.S. PATENT DOCUMENTS 9,381,041 B2 7/2016 Brown et al.
11,589,884 B2 * 2/2023 Keach ............ A61B 17/320016
2003/0120292 A1 6/2003 Park et al.
2004/0006358 A1 1/2004 Wulfman et al.
2005/0143758 A1 6/2005 Abbott et al.
2008/0208209 A1 8/2008 Fischer et al.
2010/0268029 A1 10/2010 Phan et al.
2010/0268175 A1 10/2010 Lunsford et al.
2011/0270239 A1 11/2011 Werneth
2012/0109277 A1 5/2012 Lepulu et al.
2012/0130417 A1 * 5/2012 Lepulu ............... A61B 17/3478
606/198
2017/0049457 A1 2/2017 Hays et al.
2018/0000509 A1 * 1/2018 Wilson .................. A61B 18/12
2018/0310951 A1 11/2018 Keach

FOREIGN PATENT DOCUMENTS

JP 2012-524618 A 10/2012
JP 2013-545517 A 12/2013
WO 2014/165754 A1 10/2014

OTHER PUBLICATIONS

International Search Report and Written Opinion received for PCT Patent Application No. PCT/US2018/029768, mailed on Jul. 18, 2018, 8 pages.

* cited by examiner 202
204
208
212
200

202
204
208
206
206
210
200

ENDOSCOPIC TRANSLUMINAL STENT ACCESS AND DELIVERY SYSTEM

CROSS-REFERENCE TO RELATED APPLICATION

This application is a continuation of U.S. application Ser. No. 15/963,417, filed Apr. 26, 2018, which claims the benefit of Provisional Application No. 62/491,356, filed Apr. 28, 2017, which are incorporated herein by reference in their entirety.

TECHNICAL FIELD

This disclosure relates generally to medical devices, and more specifically, to connecting two anatomical spaces of a patient for implantation of the medical devices.

BACKGROUND

Lesions of the gastrointestinal (GI) tract can be in the form of polyps that protrude from the mucosal lining with a mushroom-like shape, or flat lesions that are flush on the mucosal lining. The need to remove lesions from the mucosal lining of the GI tract is common and growing worldwide. The likelihood of having colon lesions increases with age. Approximately half of the people over the age of 60 have at least one colon lesion and often more. Some polyps are considered pre-cancerous, which means that while they are not cancerous, but if left untreated they may develop into cancer. GI tract lesions are typically found during cancer screening tests, such as a colonoscopy or flexible sigmoidoscopy.

Large resections of the colon are not typically performed endoscopically in part because tools and devices to adequately seal the resulting perforation in the colon wall are not available without approximating the defect edges which can result in lumen stricture (e.g., using clips, sutures, and the like). Such tools and devices are challenging to develop in part because of the relatively hostile colon environment that includes peristaltic movements and fecal matter.

An anastomosis is a cross-connection between two tubular tissue structures, such as blood vessels or intestines. For example, when a portion of an intestine is resected, the resulting two ends can be sewn or stapled together (anastomosed) using an intestinal anastomosis procedure. This procedure can restore intestinal continuity after the resection of a bowel portion, or to bypass a portion of unresectable diseased bowel.

Anastomoses can be created in various manners including, but not limited to: end-to-end, end-to-side, and side-to-side anastomoses. Often, suturing is used to create such anastomoses.

SUMMARY

Various aspects of the present disclosure are directed toward delivery systems. A delivery system may include a catheter having a distal end, a proximal end, and a body portion extending between the distal end and the proximal end. In addition, the delivery system may also include a tip portion arranged at the distal end of the catheter where the tip portion includes one or more cutting blades, and a plurality of struts arranged about the one or more cutting blades on the tip portion in a first configuration. The plurality of struts may be configured to actuate from the tip portion and extend from the tip portion to expose the one or more cutting blades in a second configuration.

Aspects of the present disclosure are also directed toward systems that include a delivery sheath having a lumen and a tissue penetrating a distal tip, and a tip portion configured to create an opening in the tissue. In addition, the system may include a catheter that includes a tip portion arranged at a distal end of the catheter and which has one or more cutting blades configured to enlarge the opening in the tissue, and a plurality of interconnected struts configured to independently actuate relative to the tip portion and facilitate the one or more cutting blades of the tip portion creating the enlarged opening in the tissue. Further, the catheter of the system may also include an implantable medical device arranged on the catheter proximally of the tip portion and configured to deploy within the enlarged opening.

Various aspects of the present disclosure are directed toward methods of connecting two anatomical spaces of a patient. The method may include arranging a delivery system at a target location. The delivery system, in certain instances, includes a catheter having a distal end, a proximal end, and a body portion extending between the distal end and the proximal end, a tip portion arranged at the distal end of the catheter where the tip portion includes one or more cutting blades, and a plurality of struts arranged about the one or more cutting blades. The method may also include actuating the plurality of struts distally relative to the tip portion through openings in tissue walls of the two anatomical spaces. Further, the method may include extending the tip portion through the openings in the tissue walls of the two anatomical spaces to create enlarged openings; and deploying an implantable medical device within the enlarged openings to connect the two anatomical spaces.

According to one example ("Example 1"), a delivery system includes a catheter having a distal end, a proximal end, and a body portion extending between the distal end and the proximal end; a tip portion arranged at the distal end of the catheter and including one or more cutting blades; and a plurality of struts arranged about the one or more cutting blades on the tip portion in a first configuration, the plurality of struts being configured to actuate from the tip portion and extend from the tip portion to expose the one or more cutting blades in a second configuration.

According to another example ("Example 2"), further to the delivery system of Example 1, the system also includes an atraumatic distal tip, and wherein the atraumatic distal tip interconnect the plurality of struts, and proximal ends of the plurality of struts form a proximal base having a circular perimeter.

According to another example ("Example 3"), further to the delivery system of Example 2, the plurality of struts taper inwardly from the proximal base toward the atraumatic distal tip in the second configuration.

According to another example ("Example 4"), further to the delivery system of Example 3, the one or more cutting blades on the tip portion are configured to form an opening in a tissue wall having a first diameter, and the proximal base includes a second diameter greater than the first diameter in the second configuration.

According to another example ("Example 5"), further to the delivery system of Example 4, the tissue wall includes a first side and a second side, the plurality of struts are configured to expand radially in response to extending the plurality of struts are actuated distally from the tip portion across the first side of the tissue wall to the second side of the tissue wall, and the proximal base is configured to catch the second side of the tissue wall in response to the plurality of struts being actuated proximally toward the tip portion.

According to another example ("Example 6"), further to the delivery system of Example 5, further comprising a delivery sheath configured to constrain the plurality of struts prior to extending the plurality of struts distally from the tip portion across the first side of the tissue wall to the second side of the tissue wall.

According to another example ("Example 7"), further to the delivery system of Example 1, the plurality of interconnected struts configured to expand radially relative to the tip portion.

According to another example ("Example 8"), further to the delivery system of Example 1, the system also includes a cap portion arranged between the tip portion and the plurality of struts, the cap portion being configured to actuate between a first position that covers the one or more cutting blades of the tip portion and a second position of the tip portion that exposes the one or more cutting blades.

According to another example ("Example 9"), further to the delivery system of Example 8, the tip portion includes a lock configured to hold the cap portion in the second position in response to the cap portion being actuated to the second position.

According to one example ("Example 10"), a system includes: a delivery sheath having a lumen and a tissue penetrating a distal tip, a tip portion configured to create an opening in the tissue; a catheter having: a tip portion arranged at a distal end of the catheter and having one or more cutting blades configured to enlarge the opening in the tissue to create an enlarged opening, and a plurality of interconnected struts configured to independently actuate relative to the tip portion and facilitate the one or more cutting blades of the tip portion creating the enlarged opening in the tissue; and an implantable medical device arranged on the catheter proximally of the tip portion and configured to deploy within the enlarged opening.

According to another example ("Example 11"), further to the system of Example 10, the implantable medical device includes a lumen configured to interconnect two internal spaces of a patient, the tissue penetrating the distal tip is configured to create openings in the tissue of each of the two internal spaces, and the one or more cutting blades are configured to enlarge the openings in the tissue of each of the internal spaces to create enlarged openings.

According to another example ("Example 12"), further to the system of Example 11, the two internal spaces include a distal organ and a proximal organ, and the plurality of interconnected struts are configured to: actuate distally relative to a tip portion from the proximal organ and into the distal organ through the enlarged openings, expand radially relative to the tip portion, and independently actuate proximally relative to the tip portion to arrange the tissue of the proximal organ adjacent to the tissue of the distal organ to facilitate the one or more cutting blades of the tip portion creating the enlarged openings in the tissue of the proximal organ and the distal organ.

According to another example ("Example 13"), further to the system of Example 12, the system includes an implantable medical device configured to deploy within the enlarged openings to connect the proximal organ and the distal organ, and tip portion and the plurality of interconnected struts are configured to actuate proximally through the lumen of the implantable medical device after deployment.

According to another example ("Example 14"), further to the system of Example 10, the delivery sheath is configured to constrain the plurality of interconnected struts, and the plurality of interconnected struts are configured to expand radially in response to the plurality of interconnected struts release from the delivery sheath.

According to another example ("Example 15"), further to the system of Example 10, the plurality of interconnected struts includes an atraumatic distal tip, and wherein the atraumatic distal tip interconnect the plurality of struts, and proximal ends of the plurality of struts form a proximal base having a circular perimeter.

According to another example ("Example 16"), further to the system of Example 15, the proximal base of the plurality of interconnected struts includes a diameter greater than a diameter of the opening in the tissue.

According to one example ("Example 17"), a method of connecting two anatomical spaces of a patient, the method includes: arranging a delivery system at a target location, the delivery system including a catheter having a distal end, a proximal end, and a body portion extending between the distal end and the proximal end, a tip portion arranged at the distal end of the catheter and including one or more cutting blades, and a plurality of struts arranged about the one or more cutting blades; actuating the plurality of struts distally relative to the tip portion through openings in tissue walls of the two anatomical spaces; extending the tip portion through the openings in the tissue walls of the two anatomical spaces to create enlarged openings; and deploying an implantable medical device within the enlarged openings to connect the two anatomical spaces.

According to another example ("Example 18"), further to the method of Example 17, the method also includes actuating the plurality of struts proximally relative to the tip portion arrange the tissue walls to the two anatomical spaces adjacent from one another prior to extending the tip portion through the openings.

According to another example ("Example 19"), further to the method of Example 17, extending the tip portion through the openings includes catching the one or more cutting blades within the plurality of struts.

According to another example ("Example 20"), further to the method of Example 17, the method also includes actuating the plurality of struts and the tip portion through a lumen in the implantable medical device after deploying the implantable medical device within the enlarged openings.

According to one example ("Example 21"), a delivery system includes: a catheter having a distal end, a proximal end, and a body portion extending between the distal end and the proximal end; a tip portion arranged at the distal end of the catheter and including one or more cutting blades; and a plurality of struts arranged about the one or more cutting blades on the tip portion in a first configuration, the plurality of struts being configured to actuate from the tip portion and extend from the tip portion to expose the one or more cutting blades in a second configuration.

According to another example ("Example 22"), further to the delivery system of Example 21, the delivery system also includes an atraumatic distal tip, and wherein the atraumatic distal tip interconnect the plurality of struts, and proximal ends of the plurality of struts form a proximal base having a circular perimeter.

According to another example ("Example 23"), further to the delivery system of Example 22, the plurality of struts taper inwardly from the proximal base toward the atraumatic distal tip in the second configuration.

According to another example ("Example 24"), further to the delivery system of Example 23, the one or more cutting blades on the tip portion are configured to form an opening in a tissue wall having a first diameter, and the proximal base includes a second diameter greater than the first diameter in the second configuration.

According to another example ("Example 25"), further to the delivery system of Example 24, the tissue wall includes a first side and a second side, the plurality of struts are configured to expand radially in response to extending the plurality of struts are actuated distally from the tip portion across the first side of the tissue wall to the second side of the tissue wall, and the proximal base is configured to catch the second side of the tissue wall in response to the plurality of struts being actuated proximally toward the tip portion.

According to another example ("Example 26"), further to the delivery system of Example 25, the delivery system also includes a delivery sheath configured to constrain the plurality of struts prior to extending the plurality of struts distally from the tip portion across the first side of the tissue wall to the second side of the tissue wall.

According to another example ("Example 27"), further to the delivery system of Example 26, the delivery sheath includes a tissue puncturing distal tip.

According to another example ("Example 28"), further to any one of Examples 21-27, the plurality of interconnected struts configured to expand radially relative to the tip portion.

According to another example ("Example 29"), further to any one of Examples 21-28, the delivery system also includes a cap portion arranged between the tip portion and the plurality of struts, the cap portion being configured to actuate between a first position that covers the one or more cutting blades of the tip portion and a second position of the tip portion that exposes the one or more cutting blades.

According to another example ("Example 30"), further to the delivery system of Example 29, the tip portion includes a lock configured to hold the cap portion in the second position in response to the cap portion being actuated to the second position.

According to another example ("Example 31"), further to any one of Examples 21-30, the one or more cutting blades are configured to enlarge the opening in the tissue to create an enlarged opening, and further including an implantable medical device arranged on the catheter proximally of the tip portion and configured to deploy within the enlarged opening.

According to another example ("Example 32"), further to the delivery system of Example 31, the plurality of interconnected struts configured to independently actuate relative to the tip portion and facilitate the one or more cutting blades of the tip portion creating the enlarged opening in the tissue According to another example ("Example 33"), further to the delivery system of Example 31, the implantable medical device includes a lumen configured to interconnect two internal spaces of a patient, the tissue penetrating the distal tip is configured to create openings in the tissue of each of the two internal spaces, and the one or more cutting blades are configured to enlarge the openings in the tissue of each of the internal spaces to create enlarged openings.

According to another example ("Example 34"), further to the delivery system of Example 33, the two internal spaces include a distal organ and a proximal organ, and the plurality of interconnected struts are configured to: actuate distally relative to a tip portion from the proximal organ and into the distal organ through the enlarged openings, expand radially relative to the tip portion, and independently actuate proximally relative to the tip portion to arrange the tissue of the proximal organ adjacent to the tissue of the distal organ to facilitate the one or more cutting blades of the tip portion creating the enlarged openings in the tissue of the proximal organ and the distal organ.

According to another example ("Example 35"), further to the delivery system of Example 34, the implantable medical device is configured to deploy within the enlarged openings to connect the proximal organ and the distal organ, and tip portion and the plurality of interconnected struts are configured to actuate proximally through the lumen of the implantable medical device after deployment.

DETAILED DESCRIPTION

Figure 1:
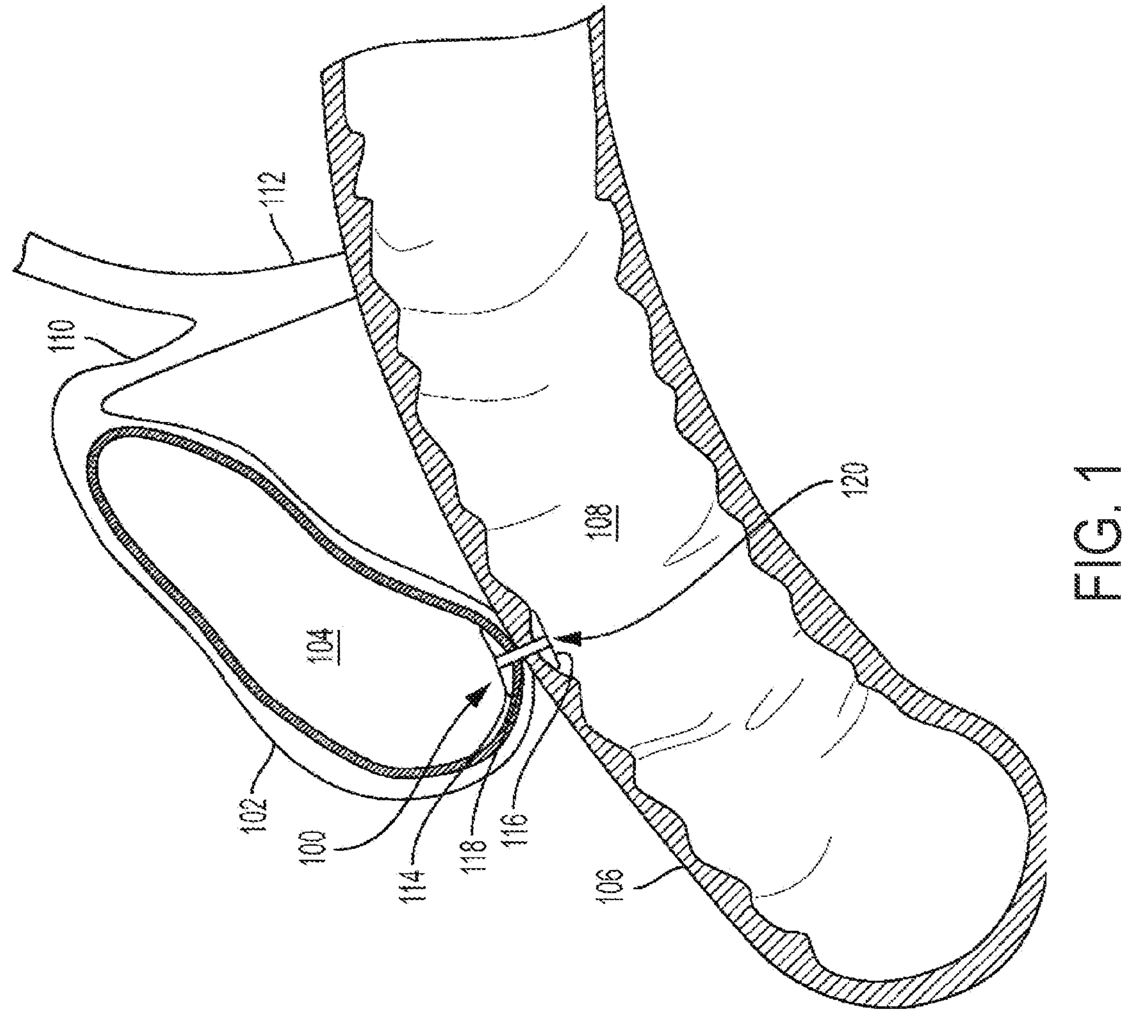
FIG. 1 shows a cutaway perspective view of an exemplary implantable medical device implanted within a patient, according to various aspects of the present disclosure.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

This disclosure provides implantable medical devices and methods for treating medical conditions using the implantable medical devices. For example, this disclosure provides implantable devices for occluding, sealing, and allowing the healing of tissue defects. Tissues that may be treated include, but are not limited to, those of the GI tract, peritoneum, vascular (arterial or venous) system, cardiac tissues, or the interface between one of these tissues and a synthetic structure such as a patch or vascular graft. Defects for which the implantable medical device may be applied include those that may be natural or artificially created, either intentionally or through some traumatic event or disease process. Defects may include, but are not limited to, perforations, ruptures, wounds, tears, endoleaks, fistulae, and the like.

Additionally, this disclosure provides, inter alia, implantable devices for connecting tissue layers, such as for connecting a gallbladder and a portion of a gastrointestinal tract to create an anastomosis that facilitates material flow therebetween. The devices are endoscopically deployable or deployable via a catheter and can include self-expanding apposition mechanism(s) that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein allow treatment to circumvent a conduit or organ blockage by creating a direct passage between tissue structures, such as, for example, the gallbladder and a portion of the gastrointestinal tract. In some embodiments, the devices provided herein are implanted temporarily. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed. Such devices can provide an alternative treatment for patients who are not suitable candidates for other types of treatment (e.g., gallbladder removal surgery) and/or to avoid known complications of other types of treatment (e.g., external biliary drainage).

In addition, aspects of the present disclosure are directed to delivery systems that facilitate transluminal placement of an implantable medical device for occluding, sealing, and allowing the healing of tissue defects. The delivery systems, consistent with various aspects of the present disclosure, allow for access between organs such that a guidewire remains inside a target organ during the procedure. In addition, the delivery systems lessen the chance of leakage from access holes that are created and into which the implantable medical device are deployed. Further, the delivery systems facilitate accurate deployment of the implantable medical device in a predictable manner.

FIG. 1 is a cutaway perspective view of an exemplary implantable medical device 100 implanted within a patient, according to various aspects of the present disclosure. The implantable medical device 100 is configured to be implanted in a patient to create a fluidic connection between spaces, tissue structures, conduits, organs, and the like, and combinations thereof. As shown in FIG. 1, for example, the implantable medical device 100 may be used to connect a gallbladder 102 (that defines an internal gallbladder space 104) with an intestine 106 (that defines an internal intestinal space 108). As a result, the implantable medical device 100 acts as a fluidic shunt device between the internal gallbladder space 104 and the internal intestinal space 108.

Such an implementation may provide a beneficial treatment to the patient when, for example, a flow blockage exists in the native anatomical conduits connecting the internal gallbladder space 104 and the internal intestinal space 108. In certain instances the patient may have one or more gallstones that cause a blockage of the patient's cystic duct 110 and/or common bile duct 112. In such a case, the implantable medical device 100 may provide a fluidic passageway such that bile from the gallbladder 102 may flow into the intestine 106.

The implantable medical device 100 may include a first end portion 114, a second end portion 116, and an intermediate portion 118 therebetween. The intermediate portion 118 defines a lumen 120 that extends longitudinally from the first end portion 114 to the second end portion 116. The lumen 120 may act as a connection (e.g., a shunt passageway) between the two spaces (e.g., tissue structures, conduits, organs) that the implantable medical device 100 connects. In the example shown in FIG. 1, the lumen 120 acts as a connection between the internal gallbladder space 104 and the internal intestinal space 108, such that the internal gallbladder space 104 is in fluid communication with the internal intestinal space 108 via the implantable medical device 100.

Although FIG. 1 shows the implantable medical device 100 connecting the gallbladder 102 and the intestine 106 of a patient, the implantable medical device 100 may be used in conjunction with various body tissue structures and organs such as, but not limited to, stomachs, colons, small intestines, pancreases, blood vessels, bladders, kidneys, and conduits.

Figures 2A, 2B:
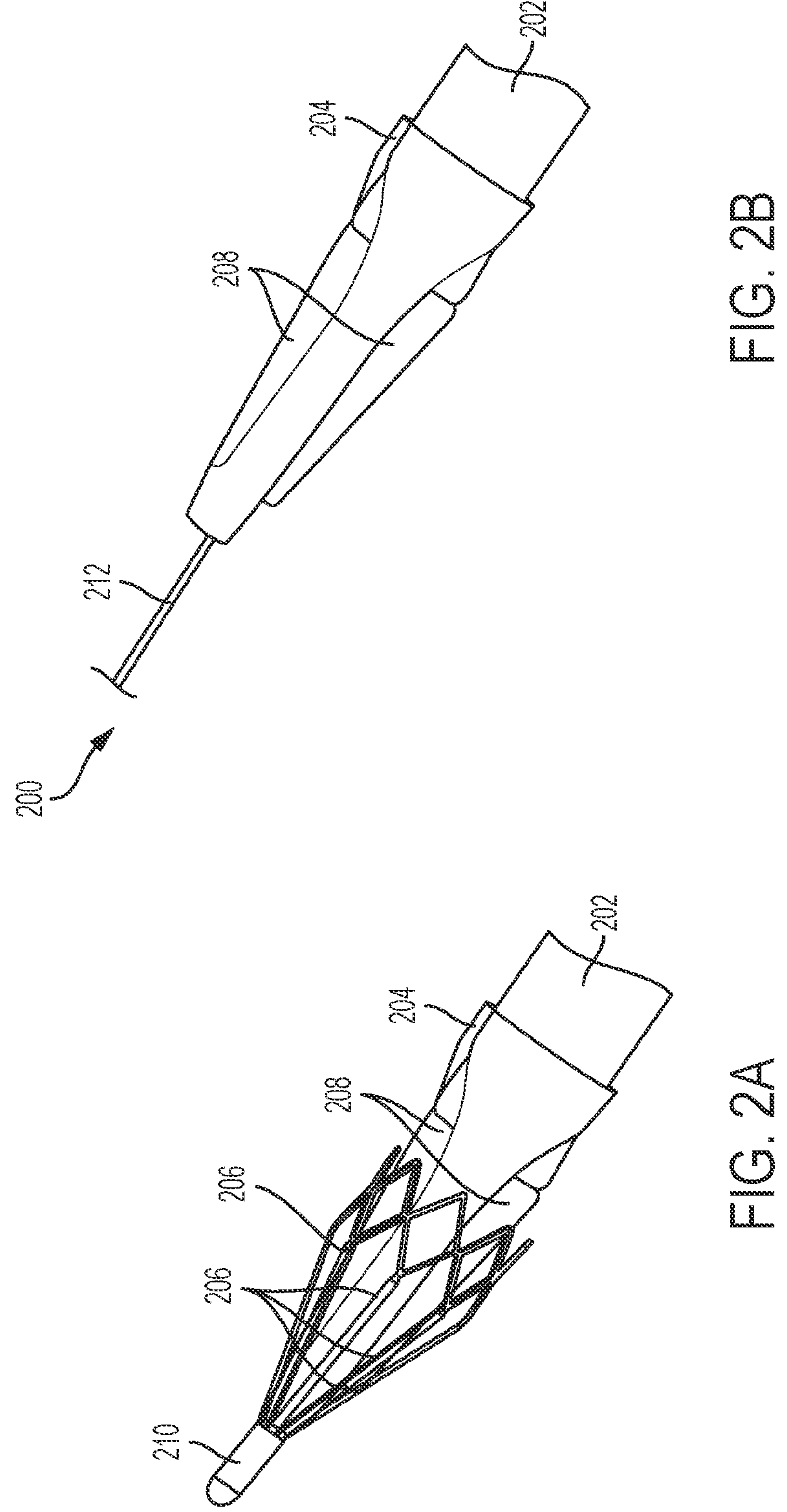
FIG. 2A shows a distal portion of a delivery system in a first configuration, according to various aspects of the present disclosure.
FIG. 2B shows the delivery system, shown in FIG. 2A, in a second configuration, according to various aspects of the present disclosure.

FIG. 2A shows a distal portion of a delivery system 200 in a first configuration, according to various aspects of the present disclosure. The delivery system 200 includes a catheter 202 having a distal end, a proximal end, and a body portion extending between the distal end and the proximal end. FIG. 2A shows the distal end portion of the catheter 202. In addition, the delivery system 200 includes a tip portion 204 arranged at the distal end of the catheter 202 and a plurality of struts 206 arranged about the tip portion 204. The plurality of struts 206 may be interconnected with one another. In certain instances, the interconnected plurality of struts 206 form a unitary structure. The interconnected plurality of struts 206 may have be basket-like structure that is configured to cover or be arranged about the tip portion 204.

The delivery system 200 delivers an implantable medical device (e.g., implantable medical device shown in FIG. 1) to connect two spaces within a patient such as spaces with organs (e.g., a gallbladder and a portion of a gastrointestinal tract). To deliver the implantable medical device to a target location and to connect the two spaces, the delivery system 200 may create openings in the tissue or enlarge openings for the implantable medical device to be deployed. In certain instances, the delivery system 200 includes one or more cutting blades 208 arranged with the tip portion 204. The one or more cutting blades 208 may be configured to penetrate tissue to create an opening in the tissue or enlarge an opening in the tissue. The plurality of struts 206 cover the one or more cutting blades 208 in a first configuration, as shown in FIG. 2A. Further and in certain instances, an atraumatic tip 210 interconnects the plurality of struts 206. A base or end portion of the plurality of struts 206 include a diameter greater than a diameter of the openings created. The cutting blades 208 may be arranged symmetrically about the tip portion 204 and may be embedded therein. The cutting blades 208 may extend a length of the tip portion 204, or, in other instances, the cutting blades 208 may extend a portion of the length of the tip portion 204. The cutting blades 208 may be arranged, relative to a perimeter of the tip portion 204, at a 35 to 60 degree angle. The cutting blades 208 may be spaced 120 degrees apart about the tip portion 204. In addition, the cutting edge of the cutting blades 208 may be tapered from distal to proximal at a nominal angle of between 5 and 25 degrees.

FIG. 2B shows the delivery system 200, shown in FIG. 2A, in a second configuration, according to various aspects of the present disclosure. The plurality of struts 206 (not shown) are configured to independently actuate relative to the tip portion 204. In certain instances, the plurality of struts 206 are coupled to an actuation wire 212 that is directly or indirectly accessible to a user of the delivery system 200. The user may apply force to the actuation wire 212 or an element coupled to the actuation wire 212 to actuate the plurality of struts 206 proximally and distally relative to the tip portion 204. Thus, and as shown in the second configuration, the one or more cutting blades 208 are exposed by the plurality of struts 206 having been moved away (distally) from the tip portion 204.

Figures 3A, 3B:
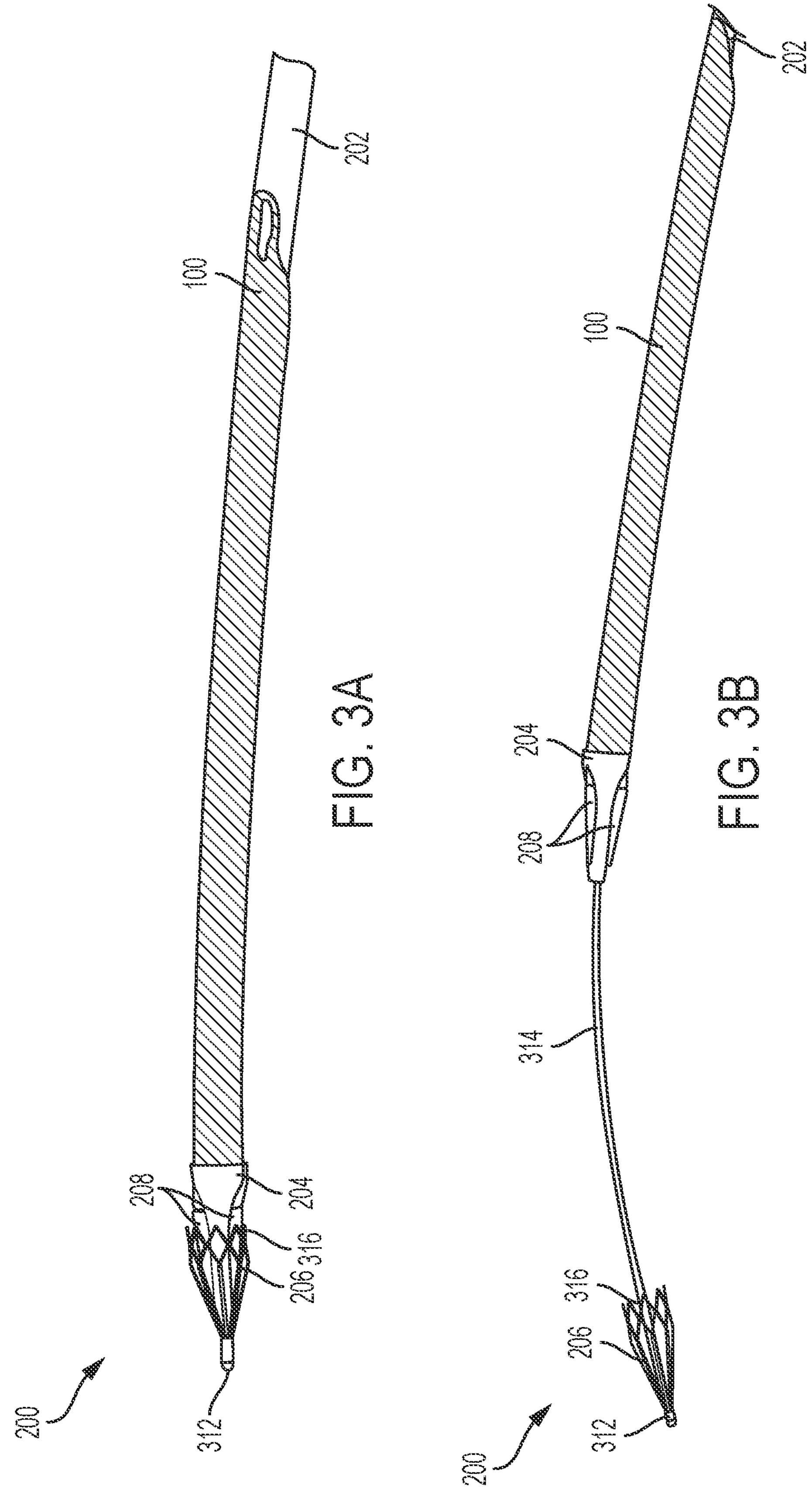
FIG. 3A shows a delivery system in a first configuration, according to various aspects of the present disclosure.
FIG. 3B shows the delivery system, shown in FIG. 3A, in a second configuration, according to various aspects of the present disclosure.

FIG. 3A shows a delivery system 200 in a first configuration, according to various aspects of the present disclosure. The delivery system 200 includes a catheter 202, a tip portion 204, and a plurality of interconnected struts 206. The catheter 202 includes a distal end, a proximal end, and a body portion extending between the distal end and the proximal end. FIGS. 3A-B show distal section of the delivery system 200. The tip portion 204 may be arranged at the distal end of the catheter 202. In addition, the delivery system 200 is configured to deliver and deploy an implantable medical device 100 (shown constrained in a delivery configuration by a constraining mechanism) to connect two spaces within anatomical structures of a patient (e.g., organs such as a gallbladder and a portion of a gastrointestinal tract). The implantable medical device 100 may be arranged or constrained on the catheter 202 in a delivery configuration for delivery of the implantable medical device 100 to a target location to connect two spaces of the patient (an example of the implantable medical device 100 in an expanded configuration is shown in FIG. 1).

The delivery system 200 may create or enlarge access locations through tissue walls of the spaces of the patient into which the implantable medical device 100 is to be deployed. The tip portion 204 of the delivery system 200 may include one or more cutting blades 208 that are configured to create an opening in a tissue wall. In certain instances and as discussed in further detail with reference to FIGS. 5A-D, an access opening is created in the tissue walls of two organs into which an implantable medical device may be delivered and deployed.

In certain instances, the plurality of interconnected struts 206 are collapsed or constrained toward the tip portion 204 in the first configuration. In this manner, the plurality of interconnected struts 206 may be advanced through the access openings in the tissue walls of the two organs. The plurality of interconnected struts 206 may include an atraumatic distal tip 312 that facilitates the passage of the plurality of interconnected struts 206 (and the delivery system 200) within the access openings in the tissue walls of the two organs. As shown in FIG. 3A, the plurality of interconnected struts 206 are arranged about the one or more cutting blades 208 in the first configuration. The plurality of interconnected struts 206 may cover the one or more cutting blades 208 to avoid unwanted damage of tissue during the endoscopic delivery procedure. The plurality of interconnected struts 206 are configured to independently actuate from the tip portion 204 and extend from the tip portion 204 to expose the one or more cutting blades 208 in a second configuration as shown in FIG. 3B.

In certain instances, the plurality of interconnected struts 206 are coupled to an actuation wire 314 to independently actuate the plurality of interconnected struts 206 relative to and from the tip portion 204. A user may manipulate the actuation wire 314 to move the plurality of interconnected struts 206 proximally and distally relative to the tip portion 204. In certain instances, the plurality of interconnected struts 206 are actuated through the access openings in the tissue walls. After the plurality of interconnected struts 206 are actuated through the access openings in the tissue walls and into a distal one of the two spaces (e.g., formed within organs) within the patient, the user may actuate the tip portion 204 against the tissue wall of a proximal (organ) one of the two spaces within the patient. The one or more cutting blades 208, having been exposed by actuation of the plurality of interconnected struts 206 to the second configuration, enlarge the access opening in the tissue wall of proximal (organ) one of the two spaces within the patient. The tip portion 204 may be further actuated to enlarge the access opening in the tissue wall of distal (organ) one of the two spaces within the patient.

In certain instances, the one or more cutting blades 208 on the tip portion 204 are configured to form an opening in a tissue wall having a first diameter and a proximal base 316 of the plurality of interconnected struts 206 has a second diameter that is greater than the first diameter. The tissue wall of both the two spaces within the patient includes a first side and a second side. In addition and as noted above, the plurality of interconnected struts 206 may be actuated through the access openings in the tissue walls prior to the tip portion 204 (and the implantable medical device 100).

In certain instances, the plurality of interconnected struts 206 may be actuated proximally back toward the tip portion 204 after being arranged within the distal one of the two spaces (within organs) within the patient. The plurality of interconnected struts 206 may move the tissue wall of the distal one of the two spaces (within organs) toward the proximal (organ) one of the two spaces. The plurality of interconnected struts 206 may be actuated until the distal (organ) one of the two spaces is moved adjacent to the proximal (organ) one of the two spaces. The user may hold the plurality of interconnected struts 206 in position (e.g., applying force proximally toward the tip portion 204) while simultaneously forcing the tip portion 204 distally toward the plurality of interconnected struts 206 to pierce the tissue walls of both the proximal (organ) one of the two spaces and the distal (organ) one of the two spaces. As a result, the one or more cutting blades 208 on the tip portion 204 enlarge the openings in the tissue walls. Subsequently, the implantable medical device 100 may be advanced within the enlarged openings in the tissue walls and deployed (e.g., as shown in FIG. 1). In this manner, the plurality of interconnected struts 206 and the tip portion 204 facilitate accurate creation of enlarged access openings in the tissue walls by preventing the delivery system 200 from misalignment or movement within the two spaces, and subsequent accurate placement of the implantable medical device 100.

In instances where the proximal base 316 of the plurality of interconnected struts 206 is larger than the (enlarged) openings in the tissue walls created by the one or more cutting blades 208, the proximal base 316 of the plurality of interconnected struts 206 facilitates creating the enlarged openings by holding the tissue walls together. For example, the proximal base 316 of the plurality of interconnected struts 206 is configured to catch a second (distal) side of the (distal) tissue wall in response to the plurality of interconnected struts 206 being actuated proximally toward the tip portion 204.

As noted above, the plurality of interconnected struts 206 are collapsed or constrained toward the tip portion 204 in the first configuration. In certain instances, the plurality of struts 206 are configured to expand radially relative to the tip portion 204. In certain instances, the delivery system 200 may be arranged through a delivery sheath (not shown) that is configured to constrain the plurality of interconnected struts 206 prior to extending the plurality of interconnected struts 206 distally from the tip portion 204. The plurality of interconnected struts 206 expand after being released from the delivery sheath.

The illustrative system shown in FIGS. 3A-B is not intended to suggest any limitation as to the scope of use or functionality of embodiments of the discussed throughout this disclosure. Neither should the illustrative system be interpreted as having any dependency or requirement related to any single component or combination of components illustrated therein. For example, in various embodiments, the illustrative delivery system 200 may include a delivery sheath as described with reference to FIGS. 5A-D. Additionally, any one or more of the components depicted in FIGS. 3A-B can be integrated with various ones of the other components depicted therein (and/or components not illustrated). For example, the delivery system 200 may be used in connection with the implantable medical device 100 shown in FIG. 1.

Figure 4B:
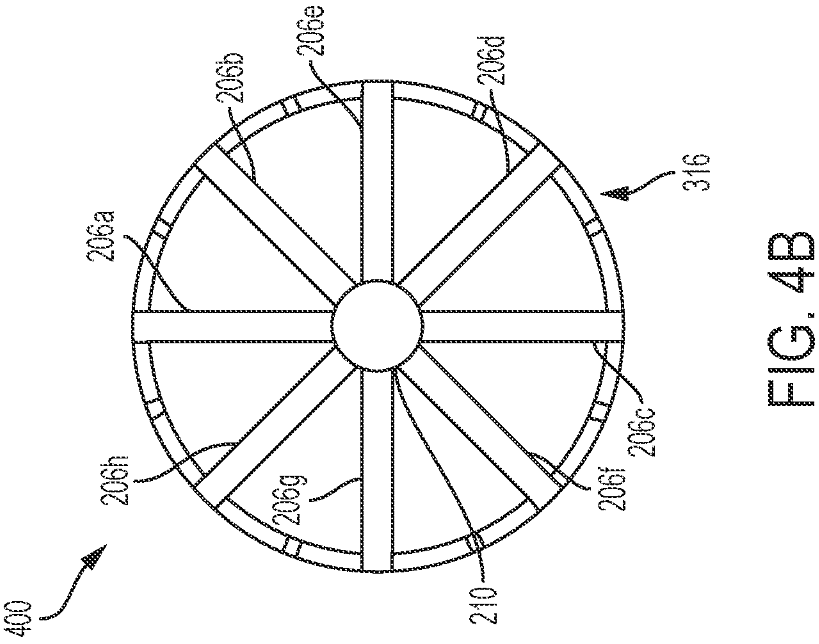
FIG. 4B shows an end view of the plurality of interconnected struts shown in FIG. 4A, according to various aspects of the present disclosure.
Figure 4A:
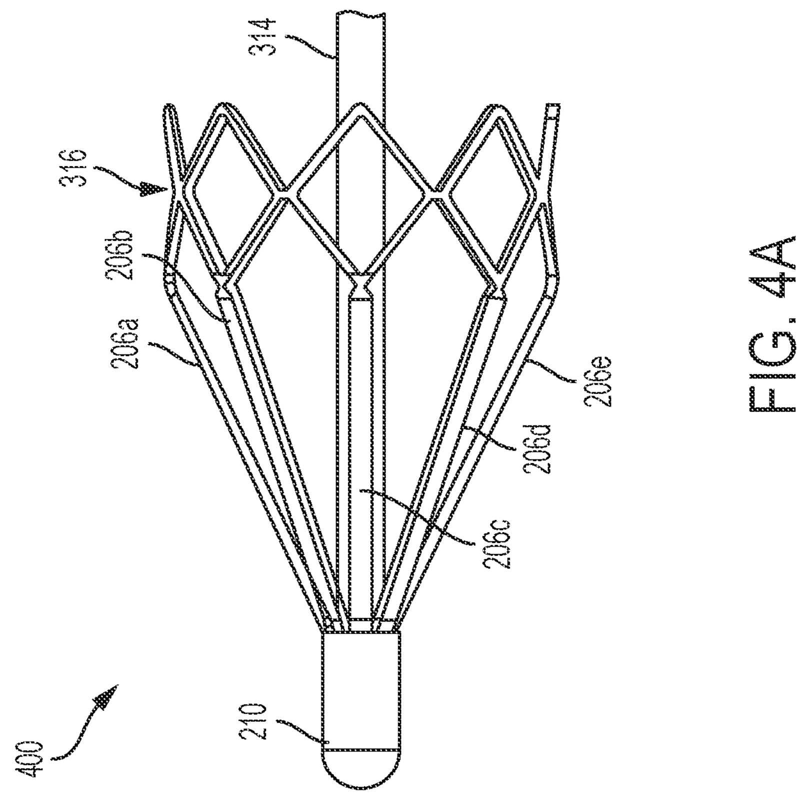
FIG. 4A shows a side view of a gripping element of a delivery system that includes a plurality of interconnected struts, according to various aspects of the present disclosure.

FIG. 4A shows a side view of a gripping element 400 of a delivery system that includes a plurality of interconnected struts 206*a-h* (struts 206*f-h* are obstructed from view in FIG. 4A), according to various aspects of the present disclosure. The plurality of interconnected struts 206*a-h*, in certain instances, are configured to cover one or more cutting blades arranged with the delivery system as shown in FIGS. 2-3. In addition, the plurality of interconnected struts 206*a-h* may be a unitary structure that is self-expanding (e.g., formed from Nitinol). For example, the plurality of interconnected struts 206*a-h* may be formed from a single structure as a cut-tube. In other instances, the plurality of interconnected struts 206*a-h* are wires that are attached to one another.

The gripping element 400 also includes an atraumatic tip 210 that interconnects the plurality of interconnected struts 206*a-h*. Further, the gripping element 400 also includes a proximal base 316 arranged at a proximal end of the gripping element 400, with the atraumatic tip 210 arranged at a distal end. The proximal base 316, in certain instances, is formed by crossing portions of the plurality of interconnected struts 206*a-h*. The crossing portions of the plurality of interconnected struts 206*a-h* in the proximal base 316 are interwoven with one another and may form diamond shaped structures about a perimeter of the proximal base 316.

As shown in FIG. 4A, the plurality of interconnected struts 206*a-h*, in certain instances, taper inwardly from the proximal base 316 toward the atraumatic tip 210. The plurality of interconnected struts 206*a-h* are coupled to an actuation wire 314. The actuation wire 314 allows for a user of the delivery system to actuate the plurality of interconnected struts 206*a-h* proximally and distally. In certain instances, the plurality of interconnected struts 206*a-h*, including the proximal base 316, may be collapsed inwardly (e.g., toward the actuation wire 314) in a delivery configuration. As further discussed below with reference to FIGS. 5A-D, the plurality of interconnected struts 206*a-h* may be collapsed to the delivery configuration by a delivery sheath, and expand after release from the delivery sheath.

FIG. 4B shows an end view of the plurality of interconnected struts 206*a-h* shown in FIG. 4A, according to various aspects of the present disclosure. The plurality of interconnected struts 206*a-h*, as shown in FIG. 4B, may be symmetrically arranged about the atraumatic tip 210 and the proximal base 316. In addition, the proximal base 316 may have a circular perimeter.

Figure 5A:
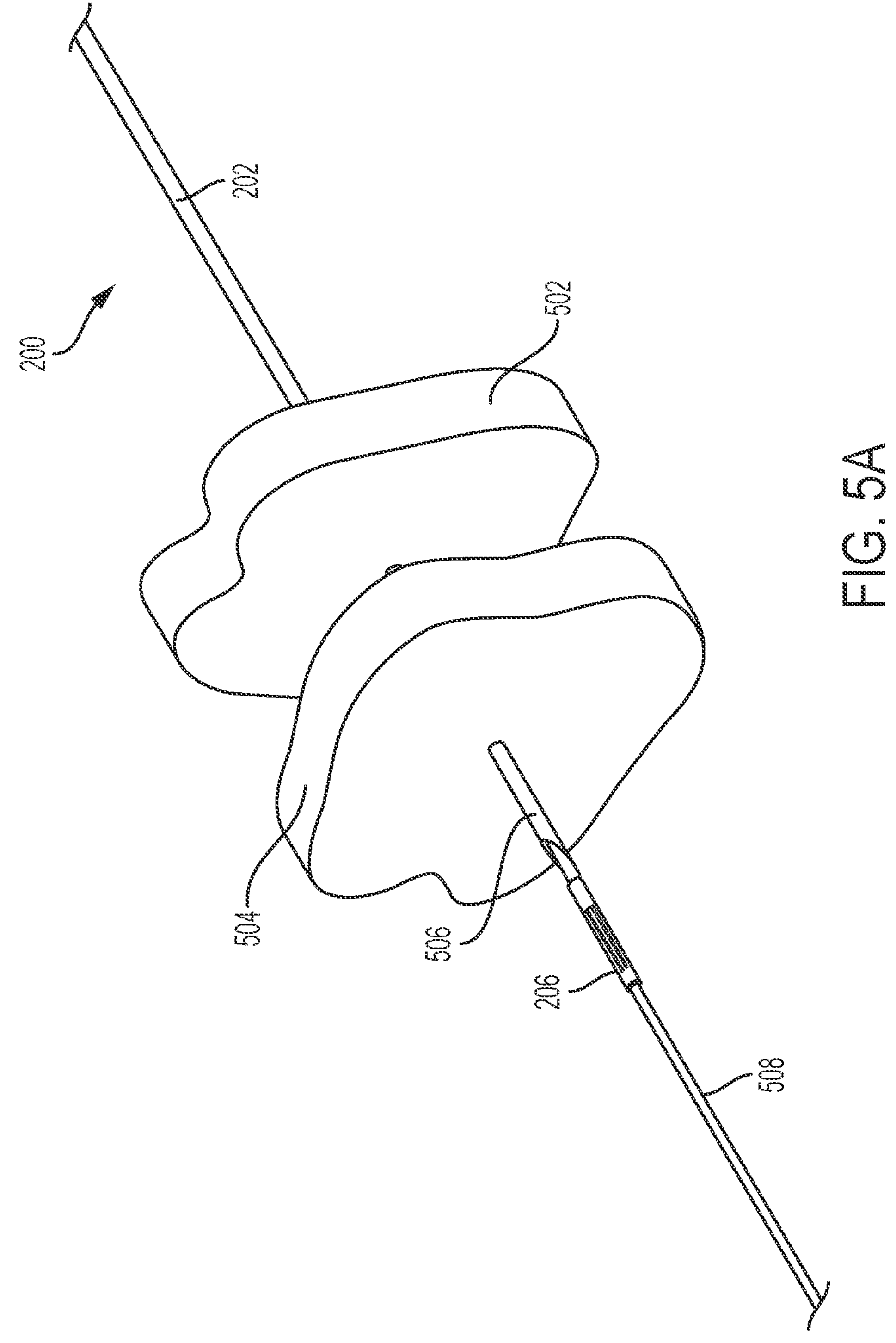
FIG. 5A shows an illustration of a step in the delivery of an implantable medical device using a delivery system, according to various aspects of the present disclosure.

FIG. 5A shows an illustration of a step in the delivery of an implantable medical device 100 (shown in FIGS. 5B-D) using a delivery system 200, according to various aspects of the present disclosure. The delivery system 200 is configured to deliver the implantable medical device 100 (shown constrained to a delivery configuration by a constraining mechanism) to connect two spaces within organs of a patient. For example, the implantable medical device 100 may be implanted to connect a portion of the patient's GI tract (such as the stomach or duodenum) and the patient's gallbladder. The delivery system 200 creates access openings in tissue walls 502, 504 at the target location. More specifically and in instances where the implantable medical device 100 is implanted to connect the duodenum and the gallbladder of a patient, the delivery system 200 may be routed through the duodenum and cross into the gallbladder of the patient.

The delivery system 200 creates an access opening (or enlarges existing openings) within the tissue wall 502 of a proximal anatomical structure (e.g., organ), and subsequently the tissue wall 504 of a distal anatomical structure (e.g., organ). As shown in FIG. 5A, a delivery sheath 506 creates access openings in each of the tissue walls 502, 504. In certain instances, the delivery sheath 506 is routed to the target location and punctures the tissue using a puncturing end of the delivery sheath 506. In other instances, the delivery sheath 506 is routed to the target location using a guidewire 508, and may include a tissue puncturing distal tip. In certain instances, the delivery sheath 506 is similar to a surgical needle used in Fine-needle aspiration (FNA). In addition, the delivery sheath 506 includes a lumen into which other portions of the delivery system 200 are arranged.

The delivery system 200 also includes a plurality of interconnected struts 206 arranged with a catheter 202. The catheter 202 may include a served wire coil at the core of the catheter 202 to increase flexibility, while allowing the transfer of axial forces down the length of the catheter 202. The core of the catheter 202 may include a plurality of strands of stainless steel wire to increase flexibility. The plurality of interconnected struts 206 are collapsed within the delivery sheath 506 in a first configuration as shown in FIG. 5A. More specifically, the delivery sheath 506 is configured to constrain the plurality of interconnected struts 206, and the plurality of interconnected struts 206 are configured to expand radially in response to the plurality of interconnected struts 206 release from the delivery sheath 506 as is shown in FIG. 5B.

Figure 5B:
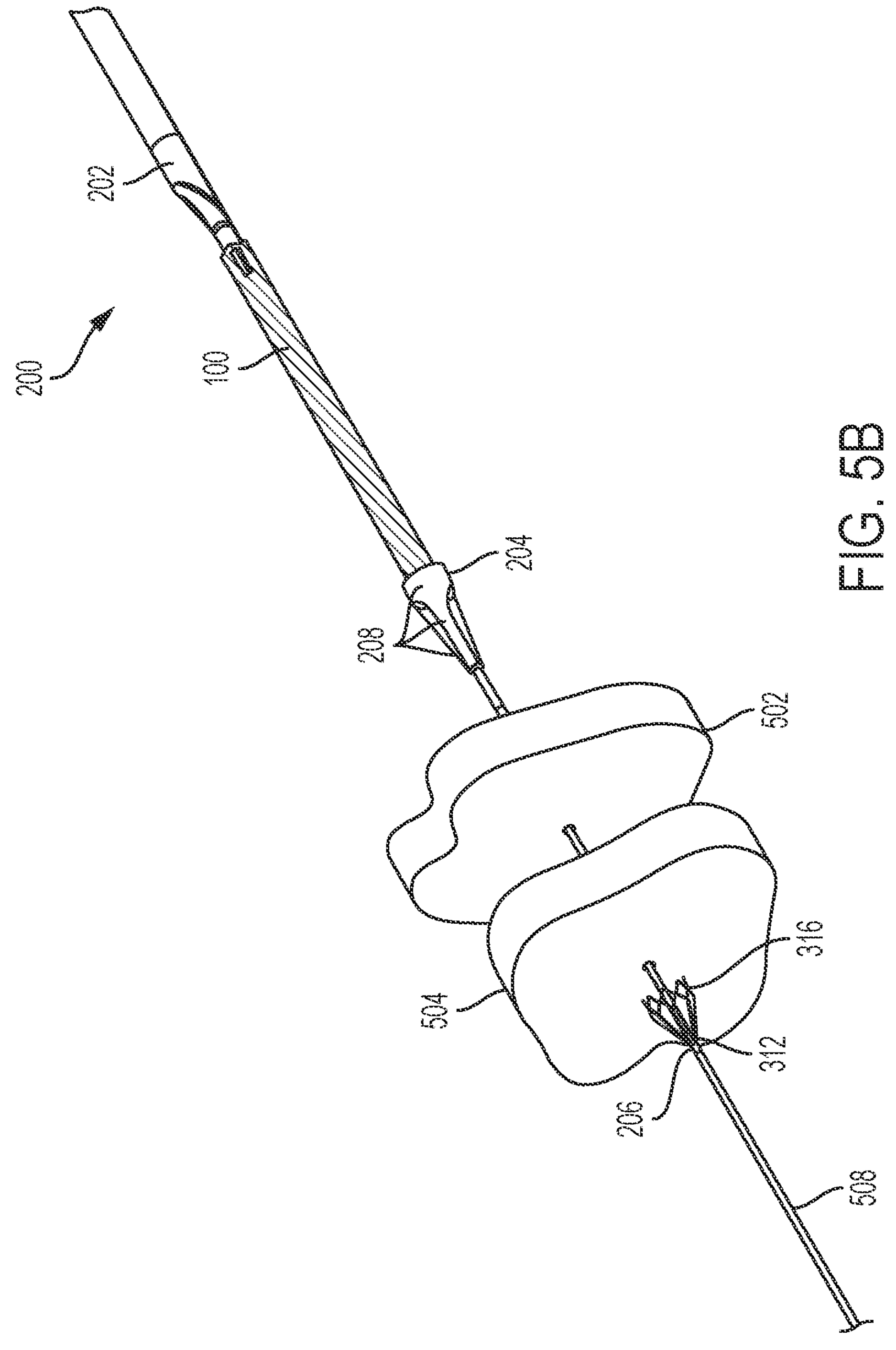
FIG. 5B shows an illustration of another step in the delivery of the implantable medical device using the delivery system, as shown in FIG. 5A, according to various aspects of the present disclosure.

FIG. 5B shows an illustration of another step in the delivery of the implantable medical device 100 using the delivery system 200, as shown in FIG. 5A, according to various aspects of the present disclosure. As shown in FIG. 5B, the plurality of interconnected struts 206 are released from the delivery sheath 506 (shown in FIG. 5A). To release the plurality of interconnected struts 206, the delivery sheath 506 may be withdrawn proximally toward the tissue wall 502 of the proximal anatomical structure. In certain instances, the plurality of interconnected struts are actuated distally to release the plurality of interconnected struts 206. In other instances, the plurality of interconnected struts 206 are actuated distally and the delivery sheath 506 may be withdrawn proximally toward the tissue wall 502 to release and expand the plurality of interconnected struts 206.

The delivery system 200 also includes a tip portion 204 arranged at a distal end of the catheter 202. The tip portion 204 includes one or more cutting blades 208. The one or more cutting blades 208 may be coupled to the tip portion 204, attached to the tip portion 204 using an adhesive, or embedded into the tip portion 204. The one or more cutting blades 208 are configured to enlarge the opening in tissue to create an enlarged opening. For example and as noted above, the delivery sheath 506 created openings in the tissue wall 502 of the proximal anatomical structure and the tissue wall 504 of the distal anatomical structure. These openings are not large enough for the deployment of the implantable medical device 100. The one or more cutting blades 208 may enlarge the openings for deployment of the implantable medical device 100.

In certain instances, use of the delivery sheath 506 to create smaller access holes in the tissue allows for precise and accurate locating of the target delivery site for the implantable medical device 100. The plurality of interconnected struts 206 help prevent the guidewire 508, and thus the delivery system 200, from unwanted shifting during creation of the enlarged access holes in the tissue walls 502, 504 and during delivery of the implantable medical device 100.

The plurality of interconnected struts 206 are configured to independently actuate relative to the tip portion 204 and facilitate the one or more cutting blades 208 of the tip portion 204 in creating the enlarged openings. The plurality of interconnected struts 206, may be actuated toward the tip portion 204, to be arranged in the tissue wall 502 of the proximal anatomical structure adjacent to the tissue wall 504 of the distal anatomical structure. In certain instances, the plurality of interconnected struts 206 includes an atraumatic distal tip 312 and a proximal base 316. The proximal base 316 of the plurality of interconnected struts 206 may include a diameter greater than a diameter of the openings created by the delivery sheath 506 (not shown in FIGS. 5B-D) in the tissue walls 502, 504. Thus, in actuating the plurality of interconnected struts 206 distally, the proximal base 316 may contact a distal side of the tissue wall 504 of the distal anatomical structure and move the tissue wall 504 of the distal anatomical structure toward the tissue wall 502 of the proximal anatomical structure.

Figure 5C:
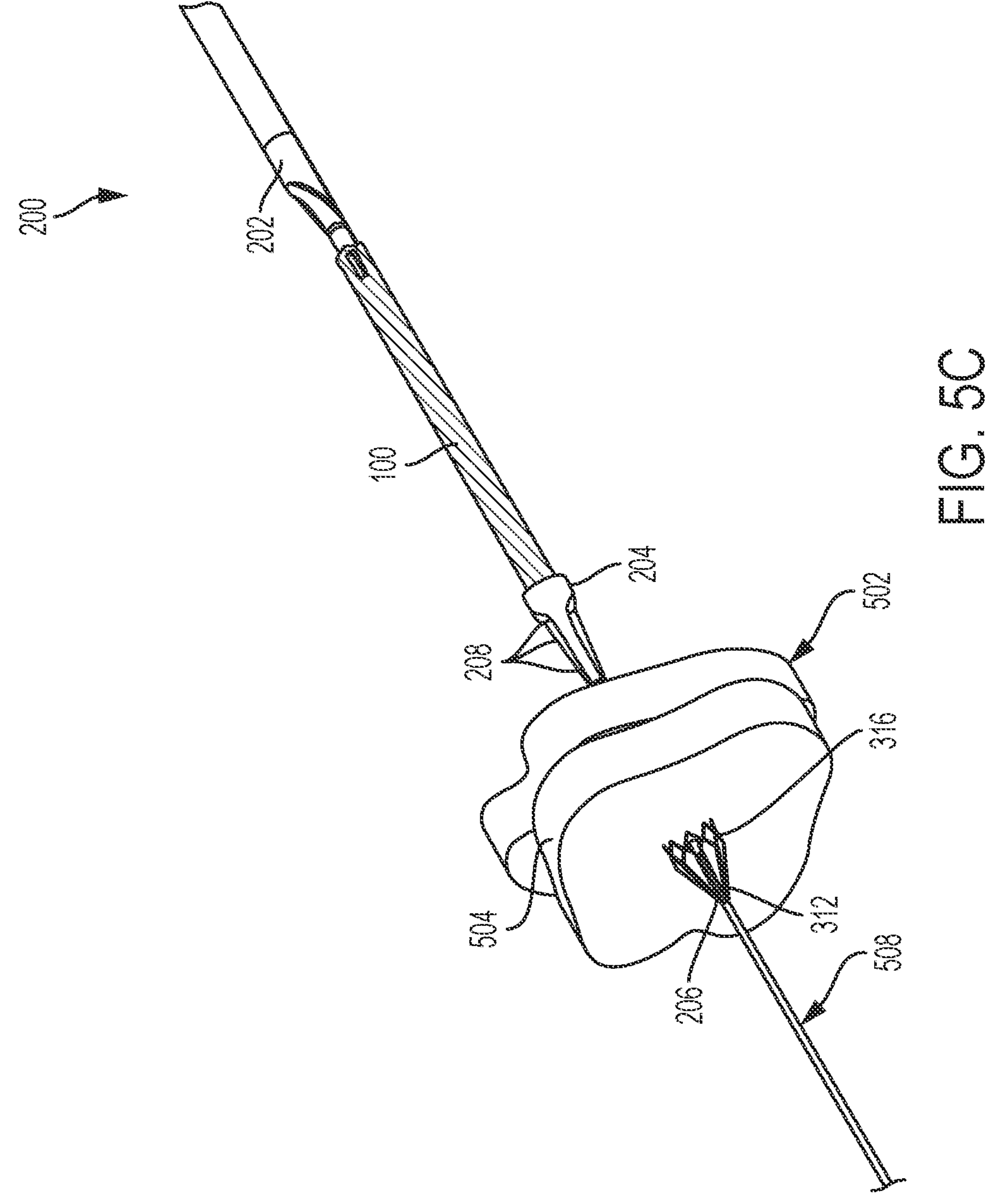
FIG. 5C shows an illustration of another step in the delivery of the implantable medical device using the delivery system, as shown in FIGS. 5A-B, according to various aspects of the present disclosure.

FIG. 5C shows an illustration of another step in the delivery of the implantable medical device 100 using the delivery system 200, as shown in FIGS. 5A-B, according to various aspects of the present disclosure. The plurality of interconnected struts 206 have been actuated, independently of and relative to the tip portion 204, the plurality of interconnected struts 206 arrange the tissue wall 502 of the proximal anatomical structure adjacent to the tissue wall 504 of the distal anatomical structure. While holding the plurality of interconnected struts 206 against the tissue wall 504 of the distal anatomical structure, the tip portion 204 may be actuated toward the plurality of interconnected struts 206. The one or more cutting blades 208 of the tip portion 204 contact a proximal side of the tissue wall 502 of the proximal anatomical structure and create an enlarged opening where the access opening was created by the delivery sheath 506. The tip portion 204 may be further actuated such that the one or more cutting blades 208 of the tip portion 204 contact the tissue wall 504 of the distal anatomical structure and create an enlarged opening where the access opening was created by the delivery sheath 506.

Figure 5D:
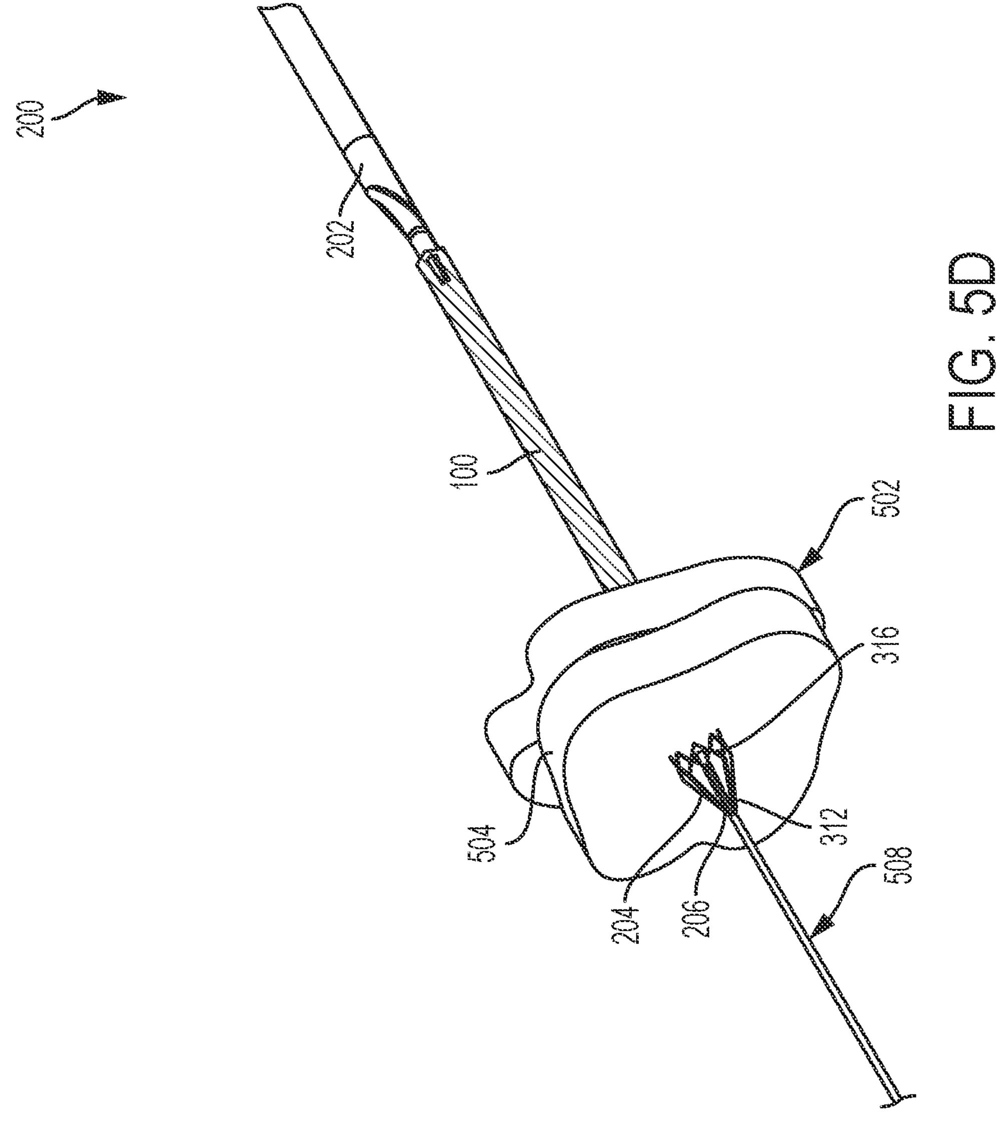
FIG. 5D shows an illustration of another step in the delivery of the implantable medical device using the delivery system, as shown in FIGS. 5A-C, according to various aspects of the present disclosure.

FIG. 5D shows an illustration of another step in delivery of the implantable medical device 100 using the delivery system 200, as shown in FIGS. 5A-C, according to various aspects of the present disclosure. As shown in FIG. 5D, the tip portion 204 has created larger openings in the tissue walls 502, 504. Due to the plurality of interconnected struts 206 and the tip portion 204 being independently actuatable, the plurality of interconnected struts 206 stabilizes the delivery system 200 during the one or more cutting blades 208 (not shown) slicing the tissue walls 502, 504.

The one or more cutting blades 208 may include three cutting blades 208 symmetrically arranged about the tip portion 204. The cutting blades 208 lessen the potential for organ leakage after deployment of the implantable medical device 100. When the catheter 202, and more particularly the tip portion 204, is pushed into the tissue walls 502, 504 and against the plurality of interconnected struts 206, the cutting blades 208 create a radial pattern of slits in the tissue walls 502, 504. The resulting flaps of tissue are pushed out of the way when the implantable medical device 100 (arranged distally of the tip portion 204 on the catheter 202) is advanced within the openings the implantable medical device 100 immediately follows behind the cutting blades 208. As a result of the implantable medical device 100 being arranged on the same delivery system 200 as the cutting blades 208, opportunity for gaps between the tissue walls 502, 504 are lessened thereby decreasing the opportunity for contents within the anatomical structures to cross and/or leak from the anatomical structures.

Further, after the tissue wall 504 of the distal anatomical structure has been opened by the one or more cutting blades 208, the plurality of interconnected struts 206 may catch the tip portion 204. The cutting blades 208 seat into the plurality of interconnected struts 206, which prevents unintentional perforations of the proximal anatomical structure that would result in content leakage. Further, the tip portion 204 seating within the plurality of interconnected struts 206 provides a tactile feedback mechanism to the user (e.g., physician) of the delivery system 200. The tip portion 204 contacting the plurality of interconnected struts 206 results in a stopping tactile indication thereby indicating that the distal anatomical structure has been accessed and helping to ensure that the implantable medical device 100 is implanted within the anatomical structures.

As shown in FIGS. 5B-D, the implantable medical device 100 is in a constrained delivery configuration. The implantable medical device 100 may be arranged in the implantable medical device 100 by use of a constraining mechanism that may be released or removed to deploy the implantable medical device 100. The constraining mechanism may be released or removed to deploy the implantable medical device 100 as shown in FIG. 1. In addition and as shown in FIG. 1, the implantable medical device 100 includes a lumen (not shown) configured to interconnect two internal spaces of the anatomical structures.

As noted above, the plurality of interconnected struts 206 independently actuate distally relative to the tip portion 204, expand radially (e.g., relative to the tip portion 204) after released from the delivery sheath 506, and independently actuate proximally relative to the tip portion 204 to arrange the tissue wall 502 of the proximal anatomical structure adjacent to the tissue wall 504 of the distal anatomical structure to facilitate the one or more cutting blades 208 of the tip portion 204 creating the enlarged openings in the tissue walls 502, 504. After the implantable medical device 100 has been deployed, the plurality of interconnected struts 206 and the tip portion 204 may be actuated, separately or together, through the lumen of the implantable medical device 100. In certain instances, the plurality of interconnected struts 206 and the tip portion 204 are actuated through the lumen of the implantable medical device 100 without reducing the diameters of the plurality of interconnected struts 206 or the tip portion 204. Thus, the tip portion 204 and the proximal base 316 may have diameters less than a diameter of the lumen of the implantable medical device 100.

The illustrative system shown in FIGS. 5A-D is not intended to suggest any limitation as to the scope of use or functionality of embodiments discussed throughout this disclosure. Neither should the illustrative system be interpreted as having any dependency or requirement related to any single component or combination of components illustrated therein. For example, in various embodiments, the illustrative delivery system 200 may include a cap portion as described with reference to FIGS. 6A-B. Additionally, any one or more of the components depicted in FIGS. 5A-D can be integrated with various ones of the other components depicted therein (and/or components not illustrated).

Figure 6A:
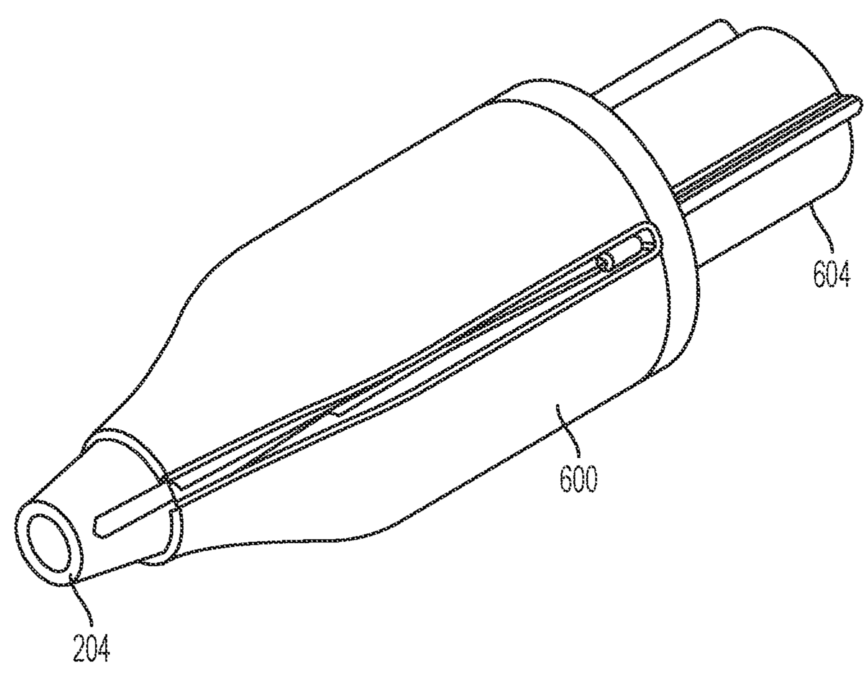
FIG. 6A shows a cap portion of a delivery system in a first position, according to various aspects of the present disclosure.
Figure 6B:
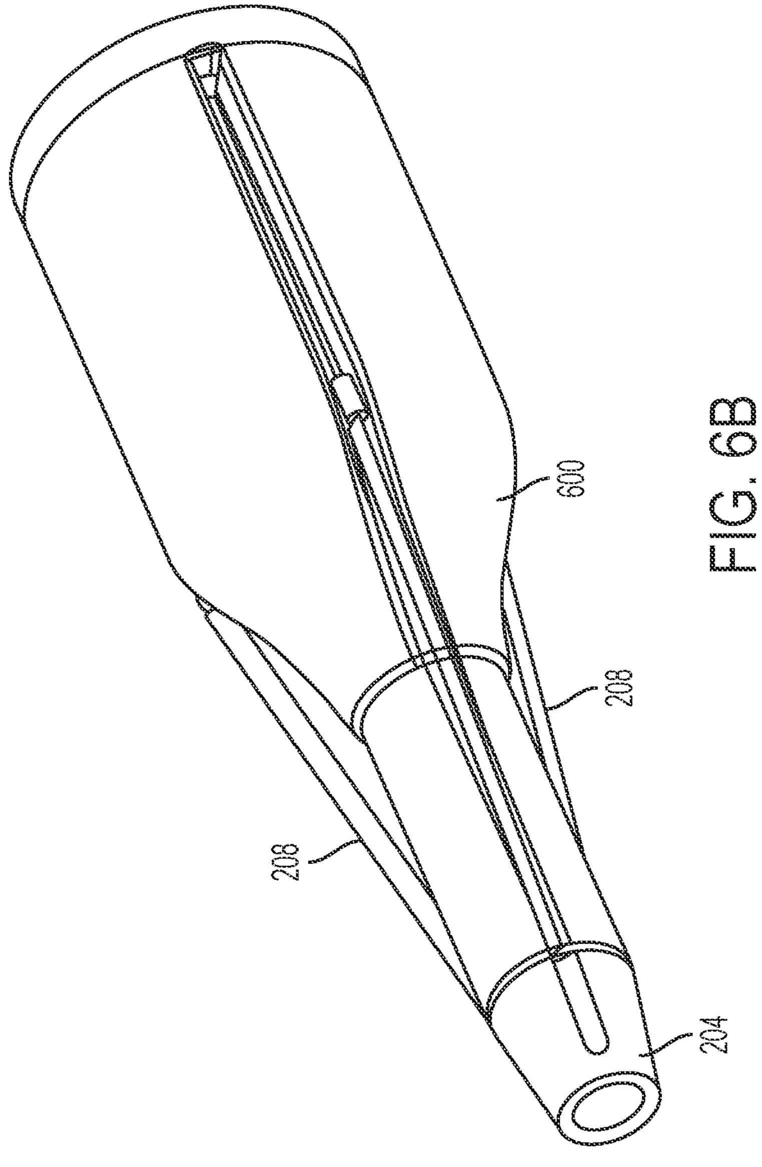
FIG. 6B shows the cap portion of the delivery system, shown in FIG. 6A, in a second position, according to various aspects of the present disclosure.

FIG. 6A shows a cap portion 600 of a delivery system in a first position, according to various aspects of the present disclosure. The cap portion 600 is coupled to a tip portion 204 of the delivery system, and in certain instances, the cap portion 600 is arranged between the tip portion 204 and a plurality of struts (e.g., as shown in FIGS. 2-5). The cap portion 600 is configured to actuate between a first position, shown in FIG. 6A, and a second position, shown in FIG. 6B. The tip portion 204 is arranged at the distal end of a catheter body 604.

As discussed above and shown in FIG. 6B, the tip portion 204 includes one or more cutting blades 208. Thus, the cap portion 600 covers the one or more cutting blades 208 in the first position, and exposes the one or more cutting blades 208 in the second position. The cap portion 600 may protect tissue from the one or more cutting blades 208 during the delivery procedure.

In certain instances, the cap portion 600 is configured to actuate between the first position and the second position based on user intervention (e.g., through an actuation wire coupled to the cap portion 600). In other instances, the cap portion 600 transitions between the first position and the second position when the cap portion 600 contacts a tissue region. As discussed in detail above with reference to FIGS. 5A-D, the one or more cutting blades 208 are configured to create an opening or enlarge an opening in tissue. As the tip portion 204 is pressed against the tissue, the tissue may force the cap portion 600 form the first position to the second position. The tip portion 204 is seated within the plurality of struts after opening the tissue, as described with reference to FIG. 5D, and thus, the surrounding tissue remains protected from the one or more cutting blades 208.

In certain instances, the cap portion 600 includes a lock configured to hold the cap portion 600 in the second position in response to the cap portion 600 being actuated to the second position. The cap portion 600 may lock in the second position based on a friction fit between the cap portion 600 and the tip portion 204. In other instances, the lock is a raised structure relative to the tip portion 204 that engages a corresponding portion of the cap portion 600 to lock the cap portion 600.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

What is claimed is:

1. A delivery system comprising:
- a catheter including a distal end, a proximal end, and a body portion extending between the distal end and the proximal end;
- a tip portion at the distal end of the catheter and including one or more cutting blades, the tip portion configured to create openings in a tissue wall of two internal spaces, the one or more cutting blades configured to enlarge the openings in tissue of each of the two internal spaces to create enlarged openings;
- a plurality of struts arranged about the one or more cutting blades in a first configuration, the plurality of struts being separable distally from the tip portion by being translated distally from the tip portion to expose the one or more cutting blades in a second configuration; and
- a leading atraumatic end connected to the plurality of struts and positioned at a terminal distal end of the delivery system in the first configuration,
- wherein a distal space is defined between the distal end of the catheter and a proximal end of the leading atraumatic end when the plurality of struts are translated distally in the second configuration.

2. The delivery system of claim 1, wherein the leading atraumatic end interconnects distal ends of the plurality of struts, and proximal ends of the plurality of struts form a proximal base having a circular perimeter.

3. The delivery system of claim 1, wherein the plurality of struts taper inwardly from the proximal base toward the leading atraumatic end in the second configuration.

4. The delivery system of claim 1, wherein the tissue wall includes a first side and a second side, the plurality of struts is configured to expand radially in response to extending the plurality of struts distally from the leading atraumatic end across the first side of the tissue wall to the second side of the tissue wall, and the proximal base is configured to catch the second side of the tissue wall in response to the plurality of struts being actuated proximally toward the leading atraumatic end.

5. The delivery system of claim 4, further comprising a delivery sheath configured to constrain the plurality of struts prior to extending the plurality of struts distally from the leading atraumatic end across the first side of the tissue wall to the second side of the tissue wall.

6. The delivery system of claim 1, further comprising a cap portion arranged between the leading atraumatic end and the plurality of struts, the cap portion being configured to actuate between a first position that covers the one or more cutting blades of the leading atraumatic end and a second position of the leading atraumatic end that exposes the one or more cutting blades.

7. The delivery system of claim 6, wherein the leading atraumatic end includes a lock configured to hold the cap portion in the second position in response to the cap portion being actuated to the second position.

8. The delivery system of claim 1, wherein the two internal spaces include a distal organ and a proximal organ.

9. The delivery system of claim 1, further including an actuation wire defining a first end coupled to the plurality of struts and a second end coupled to the catheter, wherein the actuation wire translates the plurality of struts distally from the tip portion in the second configuration.

10. The delivery system of claim 1, further comprising a delivery sheath including a lumen and a distal tip, wherein the delivery sheath is operable to releasably couple an implantable medical device to the catheter.

11. A delivery system comprising:

a delivery sheath including a lumen and a distal tip, a catheter including a distal end, a proximal end, and a body portion extending between the distal end and the proximal end;

a tip portion arranged at the distal end of the catheter and including one or more cutting blades; and a plurality of interconnected struts arranged about the one or more cutting blades on the tip portion in a first configuration, the plurality of interconnected struts being configured to actuate from the tip portion and translate extend distally away from the tip portion to expose the one or more cutting blades in a second configuration, the plurality of interconnected struts being constrained by the delivery sheath, wherein, in the first configuration, the plurality of interconnected struts cover the one or more cutting blades, and wherein a distal space is defined between the distal end of the catheter and a proximal end of the plurality of interconnected struts in the second configuration.

12. The delivery system of claim 11, wherein the plurality of interconnected struts expands radially upon release from the delivery sheath.

13. The delivery system of claim 11, further including an implantable medical device coupled to the catheter wherein the implantable medical device includes a lumen configured to interconnect two internal spaces of a patient, the distal tip is configured to create openings in tissue of each of the two internal spaces, and the one or more cutting blades are configured to enlarge the openings in the tissue of each of the internal spaces to create enlarged openings.

14. The delivery system of claim 13, wherein the plurality of interconnected struts includes a leading atraumatic end, and wherein the leading atraumatic end interconnects distal ends of the plurality of interconnected struts, and proximal ends of the plurality of struts form a proximal base having a circular perimeter, and wherein the proximal base of the plurality of interconnected struts includes a diameter greater than a diameter of the opening in the tissue.

15. The delivery system of claim 11, further including an actuation wire defining a first end coupled to the plurality of interconnected struts and a second end coupled to the catheter, wherein the actuation wire translates the plurality of interconnected struts distally from the tip portion in the second configuration.

16. A method of connecting two anatomical spaces of a patient, the method comprising:

arranging a delivery system at a target location, the delivery system including a catheter having a distal end, a proximal end, and a body portion extending between the distal end and the proximal end, an tip portion at a distal end of the catheter including one or more cutting blades, a plurality of struts arranged about the one or more cutting blades and configured to cover the one or more cutting blades in a first configuration to protect adjacent tissue from being cut by the one or more cutting blades, and a leading atraumatic end connected to the plurality of struts and positioned at a terminal distal end of the delivery system in the first configuration;

actuating the plurality of struts distally relative to the tip portion through openings in tissue walls of the two anatomical spaces such that the plurality of struts expands radially relative to the tip portion in a second configuration;

extending the tip portion through the openings in the tissue walls of the two anatomical spaces to create enlarged openings; and connecting the two anatomical spaces.

17. The method of claim 16, further comprising actuating the plurality of struts proximally relative to the tip portion to arrange the tissue walls to the two anatomical spaces adjacent from one another prior to extending the tip portion through the openings.

18. The method of claim 16, wherein the extending the tip portion through the openings includes catching the one or more cutting blades within the plurality of struts.

19. The method of claim 16, wherein connecting the two anatomical spaces is performed using an implantable medical device that facilitates connecting the two anatomical spaces.

20. The method of claim 19, further comprising actuating the plurality of struts and the tip portion through a lumen in the implantable medical device after deploying the implantable medical device within the enlarged openings.

* * * * *